United States Patent [19]

Cox et al.

[11] Patent Number: 4,935,010
[45] Date of Patent: Jun. 19, 1990

[54] DEVICES FOR SAMPLING, DRAINAGE OR INFUSION OF LIQUIDS FROM OR TO THE HUMAN OR ANIMAL BODY

[75] Inventors: Jeffrey A. Cox, West Yorkshire; Liakatali G. Parapia, Leeds, both of United Kingdom

[73] Assignee: Pharmacia Limited, Milton Keynes, United Kingdom

[21] Appl. No.: 118,606

[22] Filed: Nov. 9, 1987

[30] Foreign Application Priority Data

Nov. 20, 1986 [GB] United Kingdom ............... 8627808

[51] Int. Cl.5 .............................................. A61M 1/00
[52] U.S. Cl. ................... 604/122; 604/167; 604/905
[58] Field of Search ............. 604/167, 122, 126, 168, 604/900, 169, 905, 283

[56] References Cited

U.S. PATENT DOCUMENTS

| | | | |
|---|---|---|---|
| 3,585,996 | 6/1971 | Reynolds et al. | 604/158 |
| 4,200,096 | 4/1980 | Charvin | 128/214.4 |
| 4,424,833 | 1/1984 | Spector et al. | 604/167 |
| 4,531,937 | 7/1985 | Yates | 604/53 |
| 4,568,333 | 2/1986 | Sawyer et al. | 604/122 |
| 4,626,245 | 12/1986 | Weinstein | 604/167 |
| 4,682,980 | 6/1987 | Suzuki | 604/122 |
| 4,689,047 | 8/1987 | Bauer | 604/122 |
| 4,722,725 | 2/1988 | Sawer et al. | 604/27 |
| 4,738,668 | 4/1988 | Bellotti et al. | 604/283 |
| 4,758,225 | 7/1988 | Cox et al. | 604/167 |
| 4,784,156 | 11/1988 | Garg | 128/753 |
| 4,784,644 | 11/1988 | Sawer et al. | 604/122 |

FOREIGN PATENT DOCUMENTS

| | | |
|---|---|---|
| 0014403 | 8/1980 | European Pat. Off. . |
| 0197180 | 10/1986 | European Pat. Off. . |
| 2920975 | 11/1980 | Fed. Rep. of Germany . |
| 333922 | 12/1980 | Fed. Rep. of Germany . |
| 3100442 | 9/1982 | Fed. Rep. of Germany . |
| 1297794 | 12/1969 | United Kingdom . |
| 1277377 | 2/1970 | United Kingdom . |
| 2000976 | 1/1979 | United Kingdom . |
| 2006035 | 5/1979 | United Kingdom . |
| 2048681 | 12/1980 | United Kingdom . |

Primary Examiner—C. Fred Rosenbaum
Assistant Examiner—Mark O. Polutta
Attorney, Agent, or Firm—Fitch, Even, Tabin & Flannery

[57] ABSTRACT

A device for use in the sampling or infusion of liquids from or to the human or animal body having a first connecting means (8) for connection to a cannula, a second connecting means (13) for connection to a source or drain of liquid and valve means (4,9) operable to open or close a flow path therebetween, the arrangement being such that in a closed condition of the valve means each of the connecting means is connected to a respective chamber (6, 7), each chamber having a respective venting means (20, 21) allowing the escape of air therefrom while preventing the escape of liquid and such that in an open condition of the valve means a flow path is established from one connecting means to the other through at least one of the chambers. The device allows connection to be made without spillage and removes air from the liquid.

20 Claims, 3 Drawing Sheets

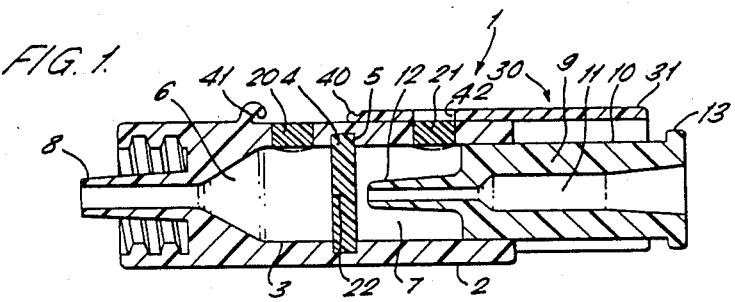

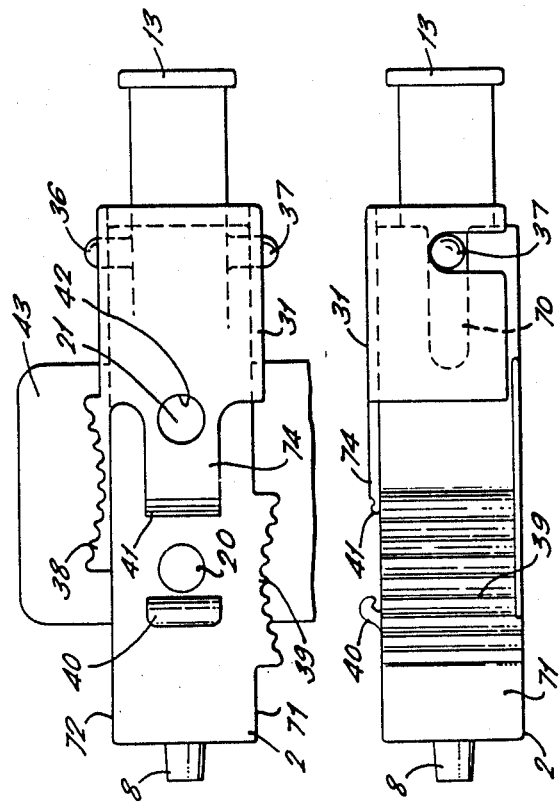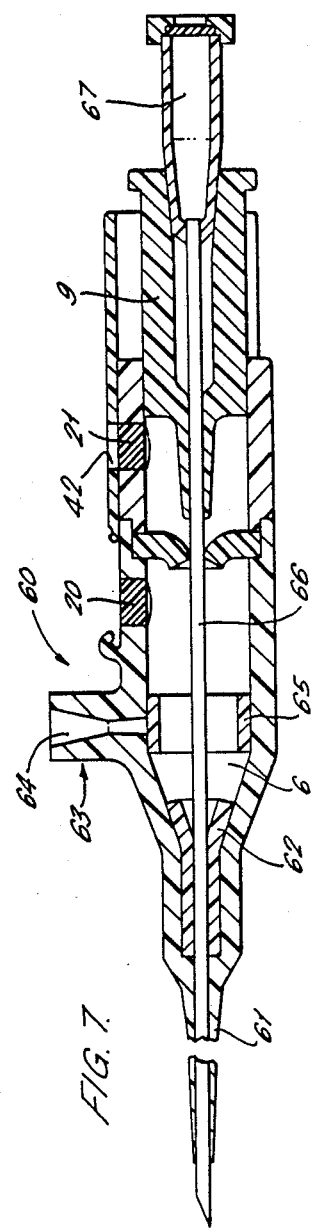

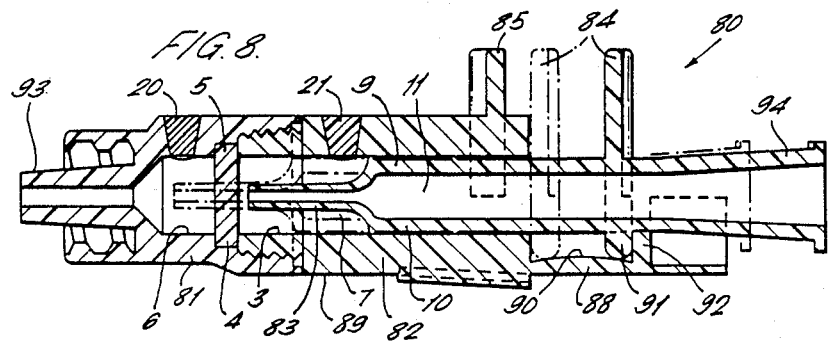
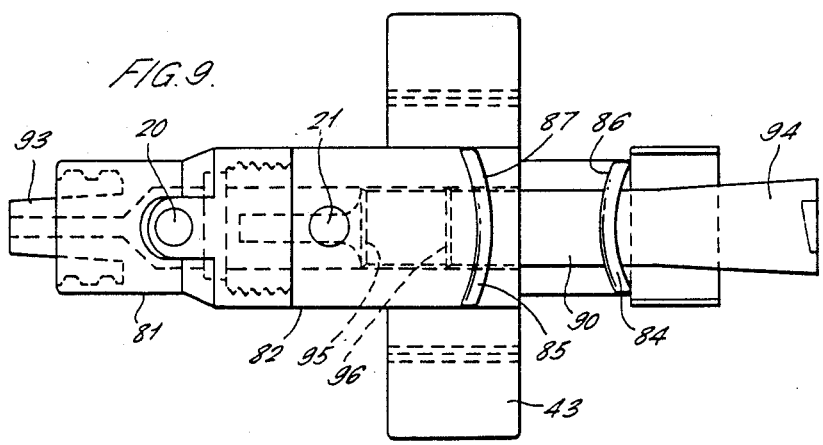
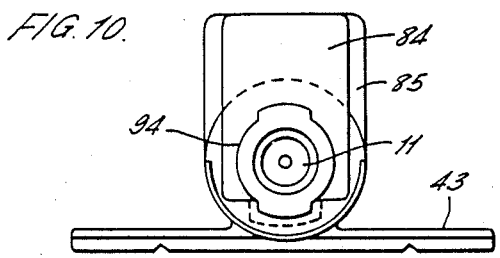

DEVICES FOR SAMPLING, DRAINAGE OR INFUSION OF LIQUIDS FROM OR TO THE HUMAN OR ANIMAL BODY

This invention relates to the sampling, drainage or infusion of liquids from or to the human or animal body and in particular but not exclusively to a device for use in intravenous infusion via a cannula.

It is known for a cannula to be used in sampling or infusion of liquids by connecting the cannula to a chamber having one or more ports through which a needle or catheter may pass into the cannula. Liquid may then be sampled or infused by connection to a drain or a source of liquid respectively by means of a catheter. It has hitherto been a problem that an air lock may develop in the chamber or in the catheter. A further problem is that liquid may be lost during coupling of components in or to the apparatus and that under certain circumstances the loss of liquid may be hazardous for example when sampling blood from the body of an infective patient or when supplying potentially irritant medication with associated hazards to the patient and operator.

According to the present invention there is disclosed a device for use in the sampling or infusion of liquids from or to the human or animal body having a first connecting means for connection to a cannula, a second connecting means for connection to a source or drain of liquid and valve means operable to open or close a flow path therebetween, the arrangement being such that in a closed condition of the valve means each of the connecting means is connected to a respective chamber, each chamber having a respective venting means allowing the escape of air therefrom whilst preventing the escape of liquid, and such that in an open condition of the valve means a flow path is established from one connecting means to the other through at least one of the chambers.

Preferably the valve means comprises an elastomeric membrane which separates one chamber from the other and which is penetrable by a co-operating ducted member to provide an open condition of the valve means and which membrane is self sealing on withdrawal of the member to provide a closed condition of the valve means.

In a preferred embodiment the ducted member defines a duct connected at one end to the second connecting means, the other end of the duct communicating in the open condition of the valve means with a first of the chambers connected to the first connecting means and in the closed condition of the valve means communicating with a second of the chambers.

Advantageously the membrane is provided with a zone of weakness to assist penetration of the ducted member when first penetrated, which zone of weakness defines a puncture site at which the membrane is punctured in use.

Conveniently the zone of weakness comprises a cruciform cut extending either partially or completely through the membrane.

Alternatively the membrane may include a preformed central puncture extending through the membrane and defining a puncture site at which the ducted member may penetrate in use.

Advantageously the membrane is radially compressed to assist self sealing on withdrawal of the ducted member.

Preferably the second chamber defines a cylindrical bore within which a piston portion of the ducted member is axially slideable, the ducted member having a ducted precursive end portion of reduced diameter extending towards and in axial alignment with the puncture site of the membrane whereby the ducted member is axially moveable into and out of penetrating engagement with the membrane.

Conveniently the precursive end portion is axially tapered towards the membrane to facilitate penetration thereof.

Conveniently the device comprises externally accessible handle means for urging the ducted member into and out of penetration with the membrane.

Advantageously the device includes locking means for selectively locking the ducted member in the membrane penetrating position.

Preferably each of the venting means comprises a hydrophobic filter comprising an air permeable barrier of a hydrophobic material. The material may be ultra high molecular weight polyethylene.

Conveniently the membrane may be of a synthetic rubber material such as silicone rubber.

Conveniently the flow path provided in an open condition of the valve means extends linearly through the device from the second connecting means to the first connecting means whereby an elongate member may extend through the chamber and cannula.

Preferably the device includes means for closing the venting means when the valve means is in the open condition. This avoids the possibility of air being drawn into the device during infusion or aspiration by negative pressure within the chambers with the consequent possibility of air bubbles entering the patient.

Particular embodiments of the invention will now be described by way of example only and with reference to the accompanying drawings in which FIG. 1 is a sectional elevation of a device having a valve means in the closed position, FIG. 2 is a similar view of the device of FIG. 1 with the valve means in the open position, FIG. 3 is a plan view of the device with the valve means in the open position, FIG. 4 is an end view of the device as viewed in the direction of arrow I of FIG. 2, FIG. 5 is a plan view of the device with the valve means in the closed position, FIG. 6 is a side view of the device as shown in FIG. 5, FIG. 7 is a sectional elevation of an alternative device having a cannula and shown in use with a trocar, FIG. 8 is a sectional elevation of a further alternative device, FIG. 9 is a plan view of the device of FIG. 8 and FIG. 10 is an end view of the device of FIGS. 8 and 9.

The device 1 of FIG. 1 comprises an elongate housing 2 of square cross section with a cylindrical bore 3 extending longitudinally through the housing. An elastomeric membrane 4 is accommodated in an annular recess 5 within the bore 3 and separates a first and second chamber 6 and 7 respectively defined by the bore.

A first connection means 8 comprises a male luer connector and is formed integrally with the housing 2 and co-axially with the bore so as to communicate with the first chamber 6. A ducted member 9 has a piston portion 10 which is a sliding fit within the second chamber 7 and defines an axially extending duct 11. A precursive portion 12 of the ducted member 9 extends towards the membrane 4 and is tapered towards the membrane. The duct 11 extends at one end through the precursive portion 12 and at its other end is enlarged to form a second connection means 13 comprising a female luer connector. The membrane 4 and the ducted member 9 together constitute a valve means the function of which will later be described.

A handle means 30 is connected to the ducted member 9 and is accessible externally with respect to the housing 2 so as to allow an operator to manually urge the ducted member towards or away from the membrane 4. The handle means 3 comprises a saddle 31 formed as a channel of U shaped cross section which is a sliding fit over the housing 2 and slideable longitudinally thereon, the saddle 31 being retained in contact with the housing by action of longitudinally extending guide ribs 32 and 33 of the housing mating with cooperating guide grooves 34 and 35 respectively formed internally on the saddle. The saddle 31 is connected to the ducted member 9 by radially extending arms 36 and 37 thereof which are slideably located in slots 70 in the sidewalls 71, 72 of the housing 2 as shown in FIGS. 5 and 6.

The handle means 30 is further provided with a saddle handle 38 extending outwardly from one side of the saddle 31 and slideably moveable therewith. A fixed handle 39 extends outwardly from the sidewall 71 of the housing 2 on the opposite side of the device to the saddle handle 38. An operator may thereby urge the saddle 31 in either direction as required along the housing 2 using a shearing motion with the saddle handle 38 and the fixed handle 39 held between thumb and index finger. The handle means 30 is further provided with locking means comprising snap engageable formations 40 and 41 mounted on the top of the housing 2 and the saddle 31 respectively.

The housing 2 is further provided at its base with laterally extending wings 43 suitable for mounting the housing on a limb of a patient using adhesive tape for example.

A first and second hydrophobic filter 20 and 21 respectively extend radially through the housing 2 so as to vent air within the first and second chambers 6 and 7 respectively to atmosphere whilst preventing the escape of liquid. The filters 20 and 21 comprise cylindrical plugs of hydrophobic material, the top of the housing 2 being cylindrically bored to accomodate the filters. The filters 20 and 21 are flush fitted with respect to the cylindrical bore 3 so as not to create any internal projection likely to foul the movement of the piston portion 10 and conversely so as not to form any recess in which a blood clot might form. The saddle 31 is provided with a circular aperture 42 which is positioned so as to overlay the second hydrophobic filter 21 when the saddle 31 is fully retracted corresponding to the closed condition of the valve means as shown in FIG. 1 i.e. when the ducted member 9 is fully withdrawn from the membrane 4. In this position of the saddle 31 any air accumulating in the second chamber 7 may be vented through the filter 21 and the aperture 42 to atmosphere. Similarly in this position of the saddle 31 the hydrophobic filter 20 is exposed to atmosphere for the venting of air from the first chamber 6.

The saddle 31 is also provided with a forward portion 74 which covers the first hydrophobic filter 20 when the saddle is moved forward to engage the locking means 40, 41 and so as to open the valve means as shown in FIG. 3. In this position the first hydrophobic filter 20 is closed by the saddle 31 and is unable to function as a vent so that air cannot enter the first chamber 6. Similarly in this position of the saddle 31 the circular aperture 42 no longer overlays the second hydrophobic filter 21 which is then closed by the saddle. In order to effect an airtight seal between the saddle 31 and the upper surface of the housing 2 a liquid film of silicone oil or grease is provided between the abutting surfaces surrounding the filters 20 and 21. In the example shown the film is provided by virtue of the saddle being formed from a lubricated grade of thermoplastic material which incorporates a proportion of silicone oil so as to form a capillary seal around the first and second hydrophobic filters 20 and 21. Alternatively a silicone based grease may be applied to conventional thermoplastic materials during assembly.

As seen in FIG. 2 the first and second hydrophobic filters 20 and 21 are closed in the open position of the valve means. This ensures that no air may be sucked into the device by any negative pressure during infusion or aspiration with consequent risk to the patient.

The membrane 4 has a central zone of weakness 22 comprising a cruciform cut extending completely through the membrane. The cruciform cut measures 3mm in each direction and the membrane 4 is of 2mm thickness. The membrane 4 is retained under radial compression within the annular recess 5.

In use to provide an infusion to a patient a cannula or needle (not shown) having a female luer connector is screw fitted to the first connection means 8. A giving set (not shown) comprising a supply of liquid infusate delivered via a plastic tube terminating in a female luer connector is prepared for connection to the device by clamping the tube to prevent the flow of liquid. The female luer connector of the giving set is then engaged with the second connection means 13 of the device 1 and the tube unclamped so that liquid passes through the tube and into the second chamber 7 by means of the duct 11. Air within the tube, the duct 11 and the second chamber 7 is displaced by liquid and vented through the second hydrophobic filter 21 and the housing 2 is positioned so that the hydrophobic filters 20 and 21 are uppermost to assist the escape of trapped air.

The cannula may then be inserted into the patient such that the first chamber 6 fills with body liquid and air displaced from the cannula and chamber 6 is vented through the first hydrophobic filter 20.

At this stage the membrane 4 and ducted member 9 together comprise a valve means which is in a closed condition. In order to commence the infusion the ducted member 9 is moved relative to the housing 2 by an operator applying a shearing motion to the handles 38 and 39 so as to move the precursive portion 12 towards the membrane. The precursive portion 12 then penetrates the membrane 4 at a puncture site 23 defined by the zone of weakness 22. Penetration is continued until the duct 11 communicates with the first chamber 6 so that a flow path is then established through the device 1 from the tube of the giving set into the second connecting means 13, the duct 11, the first chamber 6, the first connection means 8 and the cannula. In the open condition of the valve means the first and second hydrophobic filters 20 and 21 are closed against the ingress of air by the saddle 31. The ducted member 9 is retained in this position by the locking formations 40, 41.

In order to cease the infusion the ducted member 9 is moved relative to the housing 2 to retract the precursive portion 12 from the membrane 5. To achieve this a shearing motion in the reverse direction is applied to the handles 38, 39 so as to overcome the snap action of the locking formations 40, 41 and retract the precursive portion 12 from the membrane 4. The self sealing action of the membrane 4 by virtue of its elastomeric properties is assisted by radial compression within the annular recess 5 so that the valve means returns to its closed condition in which the first and second chamber 6 and 7 respectively are isolated from one another. A detachable sealing cap (not shown) is provided to externally seal the first hydrophobic filter 20 to prevent air entering the first chamber 6 during long term use with the valve means in the closed position.

In the example shown the membrane 4 is of silicone rubber of 2mm thickness. The hydrophobic filters 20 and 21 each comprise a barrier of ultra high molecular weight polyethylene in sintered porous form.

The housing 2 is of a transparent plastics material so that the filling of the chambers 6 and 7 may be observed. The radial compression of the membrane 4 is achieved by making the membrane a force fit within the recess 5.

The device may conveniently be a disposable item for use with a reusable cannula or may itself be reusable since the self sealing properties of the membrane 4 permit the valve means to operate repeatedly. In the open condition of the valve means the flow path through the device is linear so that with a catheter connected to the first connection means 8 a needle or catheter may be passed through the duct 11, the membrane 4 and hence through the cannula into the patient.

An alternative embodiment of the invention is described with reference to FIG. 7 in which those parts of the device which are common to the device of FIGS. 1 to 6 are correspondingly numbered. The device 60 of FIG. 7 includes a cannula 61 formed integrally with the housing 2 and communicating with the first chamber 6. A needle guide 62 comprising a funnel shaped insert of a low friction material such as polytetrafluoroethylene is provided at the interface between the cannula and the first chamber 6 such that a needle with a protected point inserted through the chamber is readily locatable so as to enter and extend through the cannula 61.

A bolus injection port 63 is provided in the housing 2 and communicating with the first chamber 6 which injection port comprises a tapered port 64 in the first chamber 6 which is normally sealed by a sealing ring 65 disposed circumferentially around the inside of the chamber in line with the port. A syringe (not shown) may be located in the port 64 which is tapered to provide an airtight fit. Material may then be injected from this syringe into the port 64 thereby pressurising the material sufficiently to deform the silicone seal 65 sufficiently to allow the material to be admitted into the first chamber 6. The seal 65 has a self sealing action on completion of the injection. The device is shown in use with a trocar 66 having a transparent flash back chamber 67. The trocar 66 is shown in its fully inserted position in which it extends through the first and second chambers 6 and 7 respectively and through the cannula 61 for insertion into the patient. When used to carry out an infusion into a patient the trocar 66 is inserted through the device 60 as shown in FIG. 7 and introduced into a vein of the patient until blood refluxes back into the transparent flash back chamber 67. The cannula 61 is inserted into the patient using the puncture formed by the trocar and the trocar 66 is then removed from the device with blood filling the cannula 61 and the first chamber 6. Blood spillage is prevented by the closure of the membrane 4 as the trocar 66 is withdrawn by virtue of the self sealing action of the silicone material and air is vented from the first chamber 6 through the first hydrophobic filter 20. To ensure that there is no blood loss it is necessary to check that the ducted member 9 is in its fully retracted position as is evident to the operator by the handle means 30 having longitudinally spaced apart handles 38 and 39. The giving set or unit to administer the infusate is connected to the second connection means (female luer connector) and the flow of infusate commenced so as to fill the second chamber 7. Any air in the second chamber 7 is vented through the second hydrophobic filter 21. The operator then applies shearing movement to the handle 38 and 39 so as to move the ducted member towards the membrane 4 such that the precursive portion 12 penetrates the membrane and a flow path is established through the ducted member, the membrane 4, the first chamber 6, and the cannula 61 into the patient.

The use of the handles 38, 39 to move the ducted member 9 results in minimal disturbance of the housing 2 so that the puncture site through which the cannula extends is also subject to minimum disturbance.

A further alternative device 80 is shown in FIGS. 8, 9 and 10 in which those parts of the device which are common to the device of FIGS. 1 to 6 are correspondingly numbered.

The device 80 has a forward housing portion 81 which is screw threaded to receive a rearward housing portion 82 and an annular recess 5 is formed at the interface between the housing portions. The membrane 4 is received within the annular recess 5 as in the previous embodiment.

A cylindrical ducted member 9 is axially slideable within a bore 3 within the housing 81, 82 and is integrally formed with a tubular precursive member 83.

A rearward handle 84 extends upwardly of the ducted member 9 at a location outside of the housing 81, 82 and a forward handle 85 projects upwardly of the rearward housing portion 82, the disposition of the handles being such that the ducted member 9 can be moved axially towards the rearward housing portion 82 by squeezing the handles together between the fingers and conversely the ducted member can be moved axially away from the housing by inserting a finger between the handles. To assist this latter motion the handles are shaped to provide opposing concave surfaces 86 and 87.

The rearward housing portion 82 includes a projection 88 which extends parallel to and spaced from the ducted member 9 so as to form a flat strip which is coplanar with the underside 89 of the rearward housing portion 82.

The projection 82 has an upper cammed surface 90 which cooperates with a downwardly extending detent 91 connected to the ducted member 9. A stop 92 projects upwardly of the projection 88 to define the outer limit of travel of the detent 91 and hence the outer limit of travel of the ducted member 9.

The cammed surface 90 is configured such that movement between extreme forward and rearward positions of the ducted member is opposed by interference between the cammed surface 90 and the detent 91, the result being that the ducted member is effectively locked in a forward or rearward position against being accidently moved relative to the housing.

The forward housing portion 81 is provided with a male luer connector 93 whilst the rearward housing portion 82 is provided with a female luer connector 94.

The forward and rearward housing portion 81 and 82 are provided with hydrophobic filters 20 and 21 respectively. The position of the rearward hydrophobic filter 21 is such that the ducted member 9 obturates the filter when moved into the forward position in which the precursive member 3 penetrates the membrane 4 to open the valve means constituted by the membrane 4 and the ducted member.

The forward filter 20 however continues to operate as a vent in both open and closed conditions of the valve.

To assist positive sealing between the ducted member 9 and the bore 3 the ducted member is provided with two annular seal portions 95 and 96 in the form of radial projections which are an interference fit within the bore. The forward seal 95 is located at the forward end of the ducted member 9 and the rearward seal 96 is axially spaced from the forward seal such that when the ducted member is moved to its forward position in which the valve is open the rearward filter 21 is then positioned intermediate the seals 95 and 96 and is effectively isolated.

The device 80 therefore provides a valve means which is open in a forward position of the ducted member and is closed when the ducted member is retracted such that the detent 91 contacts the stop 92. In FIG. 8 the device 80 is shown with the valve means in a closed position with a chain dot outline of the position of the ducted member in the open condition of the valve means.

A device in accordance with the present invention may also be used for the mixing of infusate immediately prior to infusion in circumstances where it is desirable to rupture a vial containing one material which it is required to mix into solution.

Typically such vials comprise a glass tube closed by a rubber septum through which a syringe needle may penetrate in order to introduce liquid material to the vial contents. A problem encountered in this procedure is that the introduction of such liquid results in a positive pressure within the vial which may produce an aerosol leakage on withdrawal of the needle. Potential hazards associated with this aerosol may be removed by use of a device in accordance with the present invention in which a device of the type shown in FIG. 1 is fitted with a needle (not shown) connected to the first connection means 8 and a syringe (not shown) containing the liquid is connected to the second connection means 13. The needle is introduced into the vial by penetration of the septum and the valve means of the device is then opened by advancing the saddle 31 to open the valve means such that the ducted member 12 penetrates the membrane 4. Liquid from the syringe may then pass through the device into the vial. Any excess pressure created within the vial may then be vented on withdrawal of the saddle 31 so as to close the valve means and open the first hydrophobic filter 20 to atmosphere thereby allowing air to escape from the first chamber 6. By means of this procedure the liquid contents are retained within the device without the formation of any aerosol leakage.

In the specific embodiments described above with reference to FIG. 7 a bolus injection port is described as a means of providing sealing action for intermittent injections. Alternative arrangements may be used such as a rubber septum through which drugs may be injected using a syringe needle, the rubber septum being self sealing on withdrawal of the needle.

A device in accordance with the present invention may comprise alternative valve means such as a duckbill valve which may function in co-operation with a suitable ducted member. Alternatively such a duckbill valve may function without the use of a ducted member in an arrangement in which the valve responds to pressure differential across the valve means to provide one way valve action.

A further alternative device may include hydrophobic filters 20 and 21 having outer surfaces which are recessed below the upper surface of the housing 2. This is an advantage when using a sealing grease material between the saddle 31 and the housing 2 and avoids the pores of the filters 20 and 21 being blocked by grease.

The membrane may in alternative embodiments include a cruciform cut which initially only partially penetrates the membrane so as to constitute a zone of weakness. The penetration is then completed when the ducted member first penetrates the cut.

We claim:

1. A device for use in the sampling or infusion of liquids from or to the human or animal body comprising:
    a housing defining a bore extending longitudinally through the housing, the housing having at one end of the bore a first connecting means for connection to a cannula, and defining a passageway communicating with the bore,
    the housing having at the other end of the bore a second connecting means for connection to a source or drain of liquid, and defining a ducted member communicating with the bore,
    valve means dividing the bore into first and second chambers and operable to open or close communication between the cannula and the source or drain of liquid and arranged such that in an open condition of the valve means communication is established from one connecting means to the other such that in use the sampled or infused liquid flows through at least one of the chambers and in a closed condition of the valve means the first and second connecting means are connected to the first and second chambers respectively, and
    the housing being further provided with first and second venting means allowing the escape of air from the first and second chambers respectively while preventing the escape of liquid therefrom.

2. A device as claimed in claim 1 including means for closing at least one of the venting means when the valve means is in the open condition.

3. A device as claimed in claim 1 wherein the flow path provided in an open condition of the valve means extends linearly through the device from the second connecting means to the first connecting means whereby an elongate member may extend through the chambers and the cannula.

4. A device as claimed in claim 1 wherein each of the venting means comprises a hydrophobic filter comprising an air permeable barrier of a hydrophobic material.

5. A device as claimed in claim 1 wherein the valve means comprises an elastomeric membrane which separates one chamber from the other and which is penetrable by a cooperating ducted member to provide an open condition of the valve means and which membrane is self sealing on withdrawal of the member to provide a closed condition of the valve means.

6. A device as claimed in claim 5 wherein the ducted member defines a duct connected at one end to the second connecting means, the other end of the duct communicating in the open condition of the valve means with a first of the chambers connected to the first connecting means and in the closed condition of the valve means communicating with a second of the chambers, and wherein the second chamber defines a ore within which a piston portion of the ducted member is axially slidable, the ducted member having a ducted precursive end portion of reduced diameter extending towards and in axial alignment with the puncture site of the membrane whereby the ducted member is axially moveable into and out of penetrating engagement with the membrane.

7. A device as claimed in claim 5 wherein the membrane is of silicone rubber.

8. A device as claimed in claim 5 wherein the first connecting means is connected to the first chamber to provide communication between the cannula and the first chamber, the second chamber comprising a ore within which the ducted member is axially slidable, one end of the ducted member being connected to the second connecting means, the other end of the ducted member comprising a ducted progressive end portion of the reduced diameter extending towards and in axial alignment with a puncture site of the membrane, and wherein the ducted member defines a duct extending through the second connecting means and the progressive portion to provide communication in the open condition of the valve means between the source or drain of liquid and the first chamber and to provide communication in the closed condition of the valve means between the source or drain of liquid and the second chamber.

9. A device as claimed in claim 5 comprising externally accessible handle means for urging the ducted member into and out of penetration with the membrane.

10. A device as claimed in claim 9 including locking means for selectively locking the ducted member in its membrane penetrating position.

11. A device for use in the sampling or infusion of liquids from or to the human or animal body comprising;

a housing defining first and second chambers;

a ducted member including a first end portion defining a preselected internal diameter and a second, ducted precursive end portion of reduced internal diameter;

valve means comprising an elastomeric membrane which separates one camber from the other and which is penetrable by the ducted member to provide an open condition of the valve means and which membrane is self-sealing on withdrawal of the member to provide a closed condition of the valve means, the membrane being radially compressed to assist said self sealing;

the membrane being provided with a zone of weakness to assist penetration of the ducted member when first penetrated, the zone of weakness comprising a cruciform cut extending through the membrane with a preformed central puncture extending through the membrane and defining a puncture site at which the ducted member may penetrate in use;

a first connecting means for connection to a cannula, and connected to the first chamber to provide communication between the cannula and the first chamber;

a second connecting means for connection to a source or drain of liquid, the second chamber comprising a bore within which the ducted member is axially slidable and one end of the ducted member being connected to the second connecting means, the second end of the ducted member being axially tapered and extending towards a puncture site of the membrane so as to be in axial alignment therewith, and wherein the ducted member defines a duct extending through the second connecting means and the precursive portion to provide communication in the open condition of the valve means between the source or drain of liquid and the first chamber and to provide communication in the closed condition of the valve means between the source or drain of liquid and the second chamber, the valve means thereby being operable to open of close a flow passageway between the cannula and the source or drain of liquid and is arranged such that in the open condition of the valve means, the first chamber, and the ducted member cooperate to form a flow passageway from one connecting means to the other, and in the closed condition of the valve means the first and second connecting means are connected to the first and second chambers respectively;

the ducted member including a piston portion intermediate the second connecting means and the precursive end portion thereof, with annular seal means being mounted on the piston portion and extending into circumferential sealing contact with the wall of the bore; and the device further comprising first and second venting means allowing the escape of air from the first and second chambers respectively while preventing the escape of liquid therefrom, the second venting means being provided in a port extending radially from the bore at a location such that the second venting means is isolated from the second chamber by the seal means and piston where the valve means is in the open position.

12. A device as claimed in claim 8 wherein the membrane include a a preformed central puncture extending through the membrane and defining the puncture site at which the ducted member may penetrate in use.

13. A device as claimed in claim 8 wherein the precursive end portion is axially tapered towards the membrane to facilitate penetration thereof.

14. A device as claimed in claim 8 including a piston portion of the ducted member intermediate the second connecting means and the progressive end portion thereof, annual seal means being mounted on the piston portion and extending into circumferential sealing contact with the wall of the bore.

15. A device as claimed in claim 14 wherein the second venting means is provided in a port extending radially from the bore at a location such that the second venting means is isolated from the second chamber by the seal means and piston where the valve means is in the open position.

16. A device as claimed in claim 8 wherein the membrane is provided with a zone of weakness to assist penetration of the ducted member when first penetrated, which zone of weakness defines the puncture site at which the membrane is punctured in use.

17. A device as claimed in claim 16 wherein the zone of weakness comprises a cruciform cut extending through the membrane.

18. A device as claimed in claim 17 wherein the membrane is radially compressed to assist self sealing on withdrawal of the ducted member.

19. A device as claimed in claim 4 wherein the material is ultra high molecular weight polyethylene.

20. A device for use in the sampling or infusion of liquids from or to the human or animal body comprising:
- a housing defining first and second chambers;
- a ducted member including a first end portion defining a preselected internal diameter and a second, ducted precursive end portion of reduced internal diameter;
- valve means comprising an elastomeric membrane which separates one chamber from the other and which is penetrable by the ducted member to provide an open condition of the valve means and which membrane is self-sealing on withdrawal of the member to provide a closed condition of the valve means;
- a first connecting means for connection to a cannula, and connected to the first chamber to provide communication between the cannula and the first chamber;
- a second connecting means for connection to a source or drain of liquid, the second chamber comprising a bore within which the ducted member is axially slidable and one end of the ducted member being connected to the second connecting means, the second end of the ducted member extending towards and in axial alignment with a puncture site of the membrane, and wherein the ducted member defines a duct extending through the second connecting means and the precursive portion to provide communication in the open condition of the valve means between the source or drain of liquid and the first chamber and to provide communication in the closed condition of the valve means between the source or drain of liquid and the second chamber, the valve means thereby being operable to open of close a flow passageway between the cannula and the source or drain of liquid and is arranged such that in the open condition of the valve means, at least one of the chambers and the ducted member cooperate to form a flow passageway from one connecting means to the other, and in the closed condition of the valve means, the first and second connecting means ar connected to the first and second chambers respectively; and
the device further comprising first and second venting means allowing the escape of air from the first and second chambers respectively while preventing the escape of liquid therefrom.

* * * * *

UNITED STATES PATENT AND TRADEMARK OFFICE
CERTIFICATE OF CORRECTION

PATENT NO. : 4,935,010

DATED : June 19, 1990

INVENTOR(S) : Jeffrey A. Cox, et al

It is certified that error appears in the above-identified patent and that said Letters Patent is hereby corrected as shown below:

In Column 3, line 13, after the word "means", change the numeral "3" to read --30--.

IN THE CLAIMS:

In Column 9, line 11, change "ore" to read --bore--.

In Column 9, line 24, change "ore" to read --bore--.

In Column 9, line 29, after the word "of" delete the word --the--.

In Column 9, line 56, change "camber" to read --chamber--.

In Column 10, line 23, change "of" to read the word --or--.

UNITED STATES PATENT AND TRADEMARK OFFICE
CERTIFICATE OF CORRECTION

PATENT NO. : 4,935,010

DATED : June 19, 1990

INVENTOR(S) : Jeffrey A. Cox, et al

It is certified that error appears in the above-identified patent and that said Letters Patent is hereby corrected as shown below:

In Column 12, line 17, change "of" to read --or--.

In Column 12, line 24, change "ar" to read --are--.

Signed and Sealed this

Sixteenth Day of July, 1991

Attest:

Attesting Officer

HARRY F. MANBECK, JR.

Commissioner of Patents and Trademarks